(12) United States Patent
Rüdinger et al.

(10) Patent No.: US 7,385,069 B2
(45) Date of Patent: Jun. 10, 2008

(54) METHOD FOR PRODUCING ISOCYANATE-ORGANOSILANES

(75) Inventors: Christoph Rüdinger, Starnberg (DE); Hans-Jürgen Eberle, Munich (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 10/595,173

(22) PCT Filed: Dec. 2, 2004

(86) PCT No.: PCT/EP2004/013722

§ 371 (c)(1),
(2), (4) Date: Mar. 17, 2006

(87) PCT Pub. No.: WO2005/055974

PCT Pub. Date: Jun. 23, 2005

(65) Prior Publication Data

US 2007/0149797 A1    Jun. 28, 2007

(30) Foreign Application Priority Data

Dec. 11, 2003 (DE) ................................ 103 58 064

(51) Int. Cl.
*C07F 7/02* (2006.01)
(52) U.S. Cl. ..................................... 556/400
(58) Field of Classification Search ..................... None
See application file for complete search history.

(56) References Cited

U.S. PATENT DOCUMENTS 3,598,852 A     8/1971   Berger
6,008,396 A     12/1999  Sheridan et al.
6,812,361 B2 *  11/2004  Kammel et al. ............ 556/414

FOREIGN PATENT DOCUMENTS

| DE | 101 08 543 C1 | 4/2002 |
| EP | 0 649 850 B1 | 1/1999 |
| EP | 1 010 704 A2 | 6/2000 |
| EP | 1 484 331 A1 | 12/2004 |
| WO | WO 02/50020 A1 | 6/2002 |
| WO | WO 02/50086 | * 6/2002 |

OTHER PUBLICATIONS

Derwent Abstract Corresponding to DE 101 08 543 C1.
Derwent Abstract Corresponding to EP 1 010 704 A2.
Derwent Abstract Corresponding to EP 1 484 331 A1.
Joachim Werther, "Fluidized-Bed Reactors", Ullmann's Encyclopedia of Industrial Chemistry, vol. 14, pp. 271-312.
Mingos et al., "The Application of Microwaves to the Processing of Inorganic Materials", British Ceramic Transactions, vol. 91, No. 4, 1992, pp. 124-127.
Orth et al., "Mikrowellenerwärmung—Anwendungen in der Industrie [Microwave Heating: Industrial applications]", elektrowärme international 49, Aug. 1991, B3, pp. 149-B-155.
A. Mühlbauer et al., "Industrielle Elektrowärmetechnik" [Industrial Electrical Heating Technology], Vulkan-Verlag, Essen, 1992. pp. V-VIII.

* cited by examiner

*Primary Examiner*—Yvonne Eyler
*Assistant Examiner*—Kellette Gale
(74) *Attorney, Agent, or Firm*—Brooks Kushman P.C.

(57) ABSTRACT

Isocyanatosilanes are prepared by themolyzing carbamatosilanes in a fluidized bed reactor containing fluidized solid particles. The process substantially avoids the deposition of solid reaction by products in the reactor.

20 Claims, 5 Drawing Sheets

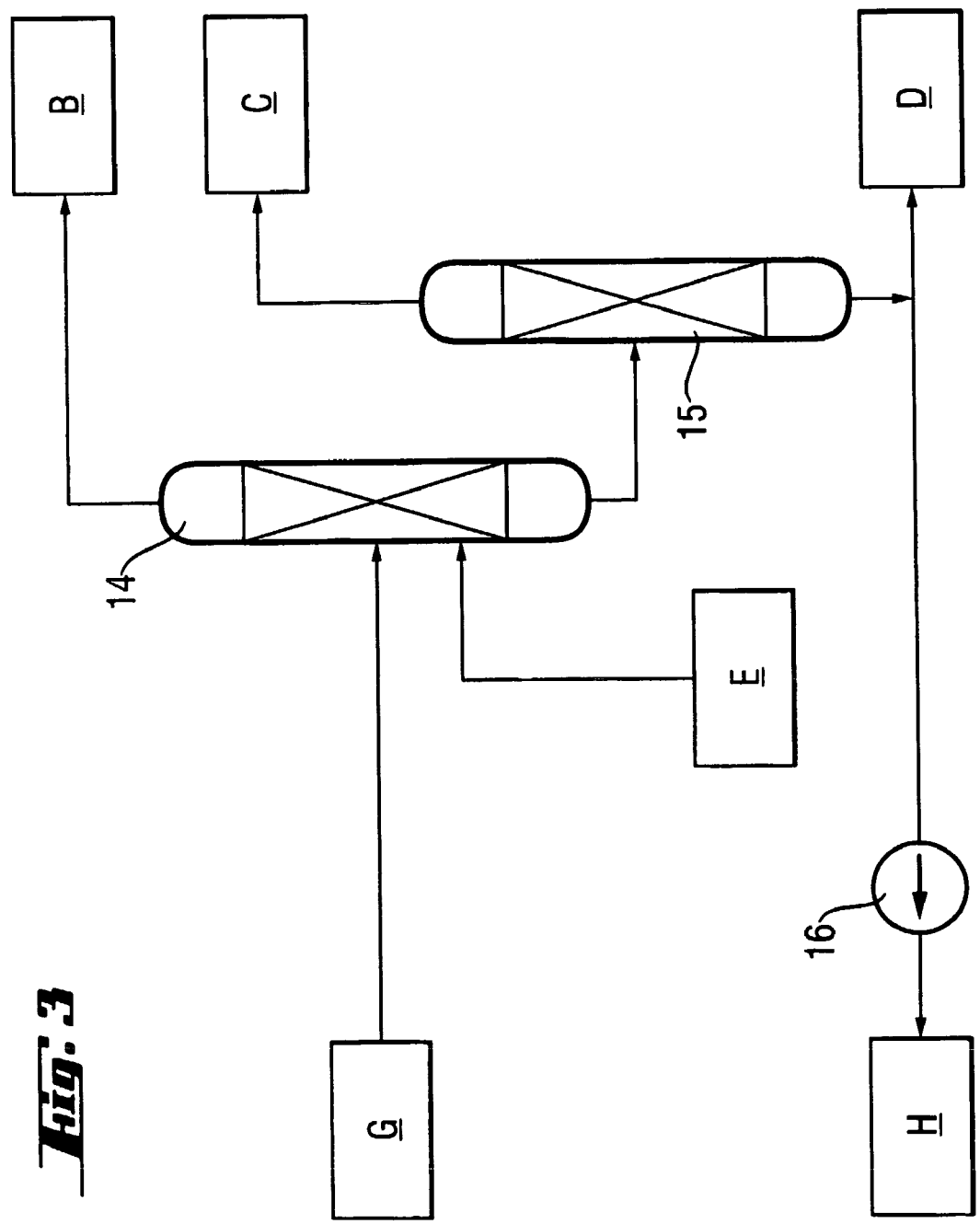

METHOD FOR PRODUCING ISOCYANATE-ORGANOSILANES

CROSS-REFERENCE TO RELATED APPLICATION

This application is the U.S. national phase of PCT Appln. No. PCT/US04/013722 filed Dec. 2, 2004, which claims priority to German application 103 58 064.6 filed Dec. 11, 2003.

BACKGROUND OF THE INVENTION

1. Field of the Invention

The invention relates to a process for preparing isocyanatoorganosilane using fluidized solid particles in a fluidized bed.

2. Description of the Related Art

For some time there has been great interest in an economic method for preparing isocyanoatoorganosilanes in high yields and purities. Such compounds are of great economic importance since they are used industrially, for example, as adhesion promoters between organic polymers and inorganic materials (also termed coupling agents, crosslinkers).

For preparation of isocyanatoorganosilanes, processes are preferred in which the starting materials substantially or completely safe in order to facilitate handling and processing. In the case of the processes previously used, however, isocyanoatoorganosilanes are prepared in relatively low amounts, and in low-efficiency and expensive processes.

For instance, in the process described in U.S. Pat. No. 6,008,396, carbamatoorganosilanes are converted in inert hot media to the isocyanates, with elimination of alcohol. However, this process can only be operated semi-continuously, since the concentration of impurities in the medium, even after a short time, increases in such a manner that the desired purity of the product is no longer ensured.

In the process described in U.S. Pat. No. 3,598,852, carbamatoorganosilanes are vaporized in vacuum and the isocyanatosilane formed is distilled off continuously.

In the process described in EP 1010704 A2 carbamatoorganosilanes are thermally cleaved in the liquid phase to give the corresponding isocyanoatoorganosilanes with catalysis by Sn(II) chloride. Particularly the highly complex process for isolating and purifying the desired products which leads to low yields has been found disadvantageous in this process, and thus it appears not to be of interest for application on an industrial scale.

EP 649850 B1 discloses the thermal cleavage (thermolysis) of carbamatoorganosilanes in the gas phase at atmospheric or reduced pressure. However, the yields obtainable by this process, in particular of isocyanatomethylorganosilanes, are unsatisfactory under the conditions described there.

In the case of all processes described in the prior art, the problem, however, is that solid deposits consisting of the products of thermal carbamate decomposition form continuously in the reaction chambers.

SUMMARY OF THE INVENTION

The An object of the invention was therefore to provide a process for preparing isocyanoatoorganosilanes by thermal decomposition (thermolysis) of carbamatoorganosilanes which substantially avoids the formation of solid deposits. This and other objects are achieved by conducting the thermolysis in the presence of fluidized solid particles.

BRIEF DESCRIPTION OF THE DRAWINGS

FIG. 3 illustrates one embodiment of a product treatment which can be used downstream of a thermolysis process.

DETAILED DESCRIPTION OF THE PREFERRED EMBODIMENT(S)

Figure 1A:
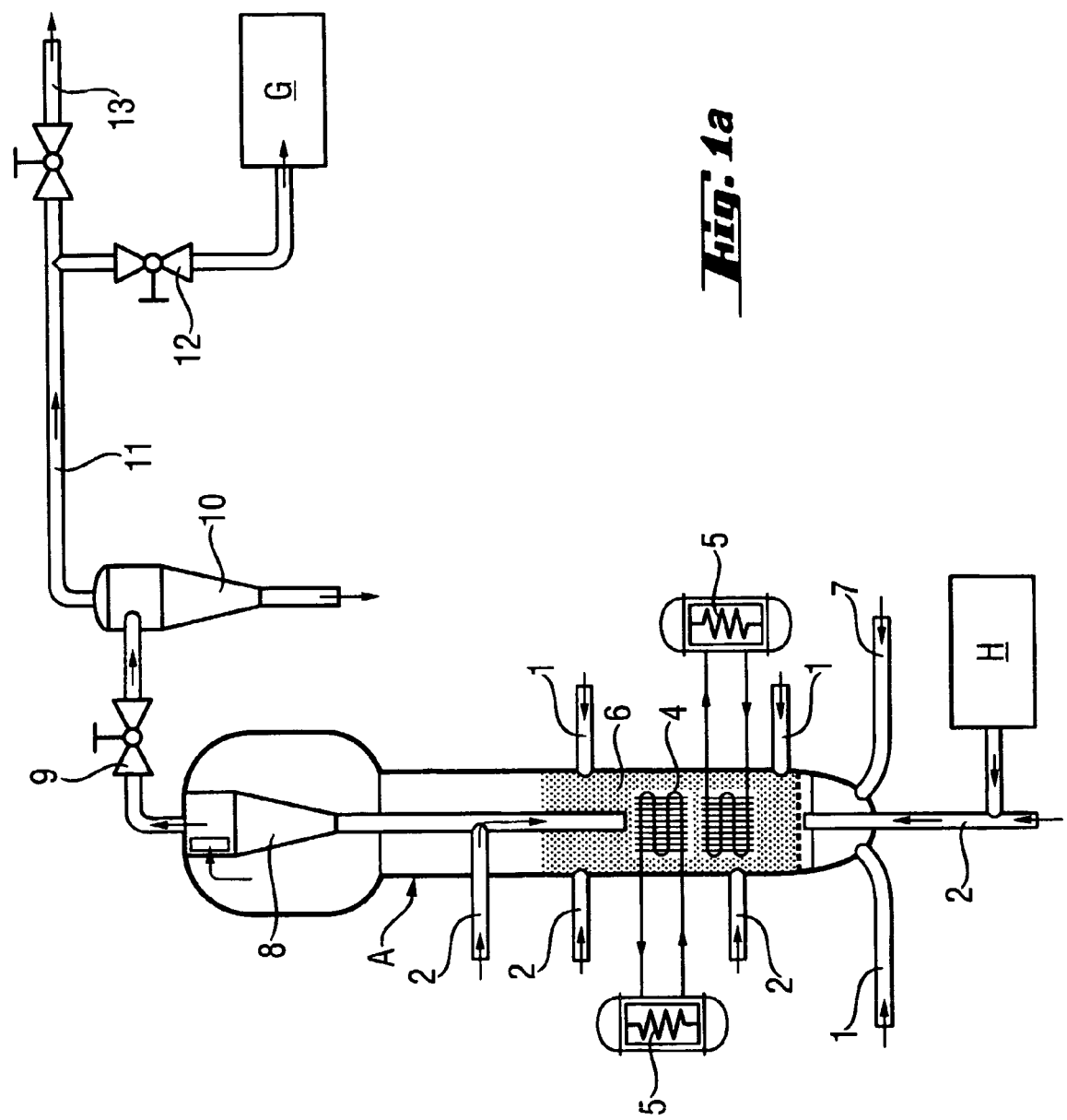
FIGS. 1a, 1b, and 1c illustrates three embodiments of a process according to the invention.

The invention relates to a process for preparing isocyanoatoorganosilanes by thermolysis of carbamatoorganosilanes in the presence of fluidized solid particles.

A preferred embodiment of the inventive process is a process for preparing isocyanoatoorganosilanes by thermolysis of carbamatoorganosilanes in the gas phase in the presence of fluidized solid particles.

The inventive process not only achieves high yields and selectivities in the preparation of the desired products, but also long operating times of the reaction units, in particular the evaporator and/or the reactor, without blockages or deposits occurring, with simultaneously low operating costs.

If carbamatoorganosilanes at high concentrations in the liquid phase are exposed to a long-lasting thermal stress, as is unavoidable in the case of heating and evaporation in conventional apparatuses such as kettle evaporators, shell-and-tube heat exchangers, shell-and-tube circulation evaporators, thin-layer evaporators, a multiplicity of unwanted decomposition reactions of the carbamatoorganosilanes occur. The decomposition reactions not only reduce the possible yield of desired isocyanatosilanes, but also lead, after a short time, to plugging of the apparatuses due to deposits together with high maintenance and servicing costs. Furthermore, the decomposition reactions which proceed unintentionally are a safety risk, since the decomposition reactions can be accelerated by heat release to the extent that, in large conventional apparatuses, a thermal explosion of the feed material can occur. Owing to the shorter residence time, less overheating of the liquid phase, and large surface area of the fluidized particles, in the inventive procedure of the process using fluidized particles, said disadvantages can be avoided. Furthermore, in the inventive procedure of the process using fluidized particles, the deposits which predominantly form on the particles can be removed without particular expenditure and thus long-lasting interference-free operation of the plant can be ensured.

The inventive process can be carried out in principle in the presence or absence of one or more homogeneous and/or heterogeneous catalysts.

In a preferred embodiment of the inventive process, isocyanoatoorganosilanes of the general formula (1) are prepared $$R^2R^3R^4Si-R^1-N=C=O \qquad (1),$$

where

R is a monovalent $C_1$-$C_{10}$-alkyl radical, $R^1$ is a divalent $C_1$-$C_6$-hydrocarbon radical and $R^2$, $R^3$ and $R^4$ are in each case independently of one another, a methyl, ethyl, n-propyl, isopropyl, methoxy, ethoxy, n-propoxy or isopropoxy radical, by thermolysis of carbamatoorganosilanes of the general formula (2)

$$R^2R^3R^4Si-R^1-NH-CO-OR \qquad (2),$$

in the presence of fluidized solid particles.

In a particularly preferred embodiment, carbamatoorganosilanes of the general formula (2) are reacted to form isocyanoatoorganosilanes of the general formula (1) in the gas phase.

In the process, alcohols of the general formula ROH are eliminated from the carbamatoorganosilanes, in particular those of the general formula (2), by thermolysis, in particular methanol, ethanol, propanol, butanol, isobutanol, pentanol, hexanol, isohexanol, cyclohexanol and 2-ethylhexanol. Preferably, methanol and ethanol, particularly preferably methanol, are eliminated.

By means of the inventive process, it is generally possible to prepare isocyanoatoorganosilanes containing short-chain spacers between the Si atom and the isocyanate function, which have been available hitherto only with difficulty and in moderate yields, in particular those isocyanoatoorganosilanes of the general formula (1) where $R^1$ is methylene.

As spacer $R^1$ between the organosilyl group and the carbamato group, use can generally be made of linear or branched saturated or unsaturated $C_1$-$C_6$-hydrocarbon groups. Preferred spacers $R^1$ are alkyl radicals, in particular linear alkyl radicals; particularly preferably, use is made of methylene, ethylene and propylene.

$R^2$, $R^3$ and $R^4$ are preferably methyl, methoxy, ethoxy, n-propoxy or isopropoxy radicals.

By means of the inventive process, in particular compounds of the general formula (1) where
$R^2$, $R^3$=methoxy, $R^4$=methyl and $R^1$=methylene; or
$R^2$=methoxy, $R^3$=ethoxy, $R^4$=methyl and $R^1$=methylene; or
$R^2$, $R^3$=ethoxy, $R^4$=methoxy and $R^1$=methylene; or
$R^2$, $R^3$=methoxy, $R^4$=ethoxy and $R^1$=methylene, can be prepared in high yields and purities.

Suitable fluidized solid particles are particles from all substances which are present at least temporarily in a solid phase under the reaction conditions.

In an advantageous embodiment of the inventive process, 1% to 100%, in particular 10% to 50%, of the fluidized solid particles consist of a catalyst or a combination of a plurality of heterogeneous catalysts. In a particularly advantageous embodiment of the inventive process, the fluidized solid particles consist of a material which can be heated to above 250° C., in particular to above 450° C., without decomposition in the presence of oxygen, in particular of air. A particularly suitable material therefore comprises non-volatile metal oxides and oxidation-resistant ceramics.

The optimum particle size depends greatly on the reactor design and on the material properties of the particles. The particles must firstly be small enough to be fluidized under the reactor conditions, and secondly must be large enough to remain in the reaction system and not be discharged.

Customarily the particle size is between $1 \cdot 10^{-6}$ m and $1 \cdot 10^{-2}$ m, advantageously between $5 \cdot 10^{-5}$ m and $5 \cdot 10^{-3}$ m, and particularly advantageously between $1 \cdot 10^{-4}$ m and $1 \cdot 10^{-3}$ m.

The particles must be abrasion-resistant enough to avoid an uneconomically high particle use owing to particle comminution.

Catalytically active particles can be introduced directly into the reaction system, or alternatively first formed in the reaction system, in particular by conversion of a catalyst precursor (precatalyst) into the catalyst or coating inert fluidized particles with catalytically active compounds in the reaction system. The fluidized particles can alternatively be impregnated with catalyst material. Likewise, the catalyst can also first be formed in the reaction system from catalyst precursors (precatalysts).

The particles and/or the heterogeneous catalyst and/or precursor compounds of the particles and/or of the heterogeneous catalysts can be fed as solution, sol, gel, emulsion, suspension, melt, vapor or solid to the reaction system batchwise or continuously, mixed with the starting material, or separately from the starting material, at one or various points of the reaction system.

The process is advantageously carried out in such a manner that, batchwise or continuously, fresh particles and/or catalyst are/is fed and, in exchange, a corresponding fraction of used particles and/or catalyst is ejected from the reaction system.

The process, in a preferred embodiment, is carried out in such a manner that the catalyst, the catalyst precursor compounds, or particle precursor compounds are present in soluble form. The homogeneous catalyst, one or more soluble catalyst precursor compounds, or one or more soluble particle precursor compounds are then either added to the reaction system dissolved in the starting material, or fed as a separate solution to the reaction system batchwise or continuously.

In an alternative embodiment, the catalyst, the particles, the catalyst precursor compounds, or particle precursor compounds, in the case of insoluble catalysts and/or particles and/or catalyst precursor compounds and/or particle precursor compounds, can be in emulsified or suspended form and fed batchwise or continuously to the starting material before entry into the reaction system.

The inventive process can optionally be carried out in the presence of a catalyst. Catalysts which come equally into consideration are in principle homogeneous and heterogeneous catalysts.

Suitable homogeneous catalysts are one or more compounds selected from the group consisting of soluble tin, lead, cadmium, antimony, bismuth, titanium, zirconium, niobium, iron, cobalt, manganese, chromium, molybdenum, tungsten, nickel, copper and zinc compounds, and also soluble organic nitrogen bases.

In particular, suitable compounds are 1,4-diazabicyclo-(2,2,2)octane, dibutyltin dilaurate, dibutyltin maleate, dibutyltin diacetate and dimethyltin dichloride.

As heterogeneous catalysts, use can be made in general of metals and/or compounds comprising elements selected from the group Sn(I), Sn(II), Pb(II), Zn(II), Cu(I), Cu(II), Co(I), Co(II), Na, K, Li, Rb, Cs, Sr, Ba, Mg, Ca, Cr, Mo, Ti, V, W, Ce, Fe, Ni, Si, Al, Ge, Ga, In, Sc, Y, La, lanthanides, Pd, Pt, Co, Rh, Cu, Ag, Au, Zn, Cd, N, B, C, and their mixtures and alloys comprising the abovementioned elements.

Preferred heterogeneous catalysts are oxides, hydroxides, oxyhydroxides, mixed oxides, acetates, formates, oxalates, tartrates, citrates, nitrates, carbonates, or mixtures of the abovementioned compounds of one or more elements selected from the group consisting of Sn(I), Sn(II), Pb(II), Zn(II), Cu(I), Cu(II), Co(I), Co(II), Na, K, Li, Rb, Cs, Sr, Ba, Mg, Ca, Cr, Mo, Ti, V, W, Ce, Fe, Ni, Si, Al, Ge, Ga, In, Sc, Y, La, lanthanides, Pd, Pt, Rh, Cu, Ag, Au and Cd.

In particular, suitable heterogeneous catalysts are those comprising one or more compounds selected from the group consisting of $TiO_2$, $ZrO_2$, $HfO_2$, $Al_2O_3$, $BaO$, $CaO$, $MgO$, $CeO_2$, $La_2O_3$, $Y_2O_3$, $Sm_2O_3$, $Yb_2O_3$, $Cr_2O_3$, $ZnO$, $V_2O_4$, $MnO_2$, $NiO$, $In_2O_3$, $Ga_2O_3$, $GeO_2$, $FeO$, $Fe_2O_3$, $Fe_3O_4$, $CuO$, $CO_3O_4$, $Fe(MoO_4)_3$, MgO/CsOH, MgO/NaOH, aluminosilicates, in particular zeolites in different pore sizes, cordierite of the composition $2MgO.2Al_2O_3.5SiO_2$, heteropolyacids, carbon modifications, e.g. graphite, transition metal nitrides, transition metal borides, transition metal silicides and carbides.

These metals, metal compounds or their mixtures can also be applied to porous or non-porous support materials. Particularly suitable supports made of inert refractory materials are oxidic and non-oxidic ceramic, $SiO_2$, carbon, aluminosilicates, magnesium aluminosilicates or resistant metallic materials, in particular glass wool, quartz wool, ceramics, oxidic compositions, such as $SiO_2$, $Al_2O_3$, $Fe_2O_3$ or steatite.

The catalyst supports can be used in the form of irregular granules, spheres, rings, half-rings, saddles, cylinders, trilobe or monoliths.

The process is generally carried out in reactors which are suitable for reactions with fluidized solid particles, in particular those in which particles can be fluidized and which simultaneously prevent the discharge of particles from the reactor. Suitable reactors having various forms of fluidized solids such as a fluidized bed, expanded fluidized beds or circulating fluidized beds are, e.g., the reactors for the methylchlorosilane direct synthesis in the fluidized bed, the fluidized-bed-cracking of petroleum fractions or "riser/regenerator" reactors, such as are used, e.g., for "fluidized catalyst cracking" (see, e.g., "Ullmann's Encyclopedia of Industrial Chemistry", Vol. B4 "Fluidized-Bed Reactors").

Suitable materials for the reactor are chemically resistant materials, in particular glass, ceramics or metals.

Depending on the reaction temperature, the energy for the reactor and/or the reaction system and/or the heating of the fluidized particles is advantageously supplied by steam, thermal oil, liquid or vaporous synthetic heat carriers, liquid salt mixtures, liquid metal alloys, hot gases, electrical resistance heating or microwave heating. In a preferred embodiment of the inventive process, the energy is supplied by means of microwave radiation.

The term "microwaves" is taken to mean here electromagnetic oscillations having a frequency of 300 MHz to 300 GHz.

The reaction chamber can be free or provided with internals. The internals affect the flow distribution, temperature distribution, and in the case of microwave heating, also the microwave distribution, in the reaction chamber. The internals can in this case consist of microwave-transparent material such as microwave-transparent glasses, quartz glass, microwave-transparent oxidic ceramic, microwave-transparent non-oxidic ceramic and then affect only the fluid flow in the reaction chamber. If the internals consist of microwave-reflecting material (e.g. high-conductivity metals, graphite) or microwave-absorbent materials (especially ceramics, silicon carbide, magnetic materials or electric resistance materials), the microwave distribution and temperature distribution are also affected.

In the reaction system, when the inventive process is optionally carried out in the presence of a catalyst, one or more of the abovementioned heterogeneous catalysts can be present or introduced continuously, together with the internals or alone.

The reaction system can also be constructed in such a manner that the entire reaction system or a part of the reaction system is filled with a fluidized solid, the solid being able to act as microwave absorber, heat carrier and/or catalyst.

For the general design of microwave irradiation systems, reference may also be made at this point to literature such as A. Mühlbauer, "Industrielle Elektro-wärmetechnik" [Industrial Electrical Heating Technology], Essen Vulkan-Verlag, 1992; D. M. P. Mingos, "The Application of Microwaves to the Processing of Inorganic Materials", British Ceramic Transactions, 91, 1992; G. Orth, "Mikrowellenerwärmung in der Industrie" [Microwave Heating in Industry] RWE-Industrieforum, Essen, 1993.

The process can be carried out batchwise, semi-continuously, or continuously. Preference is given to continuously taking off one or more volatile reaction products from the reaction system, continuous distillation of one or more volatile reaction products from the reaction system, both the reaction product alcohol and the reaction product isocyanatoorganosilane being able to be distilled off separately or together.

Used fluidized solids, with the term "used" generally being taken to mean material which has changed in properties from the initial state to the extent that it is no longer suitable for the process, in particular deactivated catalyst particles, agglomerated particles, comminuted particles, can be, continuously or batchwise, ejected from the reaction system, replaced and/or regenerated. All or a part of the particles and catalysts taken off can be regenerated.

The carbamatoorganosilane, in particular one of the general formula (2), is preferably heated in a temperature range of the fluidized solid of 150-800° C., more preferably between 200 and 600° C., and most preferably in a range of 250-500° C.

The process can be carried out with or without carrier gas. The carrier gas is preferably selected from the group consisting of nitrogen, hydrogen, air, noble, gases such as helium or argon, or vapors of carbonaceous substances such as carbon monoxide, carbon dioxide, methane, octane, toluene, decalin, tetralin or mixtures of one or more of the abovementioned gases. The component functioning as carrier gas can also be added in liquid form and is then first vaporized in the heated zone with formation of a gas stream. By means of the carrier gas, it is possible to dilute, heat or cool the reaction mixture, fluidize and/or transport solids and set defined flow conditions.

The process is preferably carried out in a pressure range of $0.01 \cdot 10^5$ Pa to $200 \cdot 10^5$ Pa, more preferably at $0.5 \cdot 10^5$ Pa to $40 \cdot 10^5$ Pa.

In the inventive process the starting material is preferably introduced into the reaction system via atomization.

The inventive process is preferably performed in such a manner that in a zone which is provided with heating devices and in which the particles are prefluidized by a gas stream, the starting material or starting material mixture comprising one or more catalysts or catalyst precursor compounds is added via nozzles in finely divided form. The vapors formed by the vaporization lead to a sharp increase in the gas stream and an additional fluidization of the particles. The starting material atomization device is, in a preferred embodiment, additionally cooled.

The inventive process, compared with the processes known from the prior art, has the great advantage that the desired products can be obtained in a simple downstream distillation step in high purity (>97%). The formation of six-membered isocyanurates observed at high thermal stresses is virtually completely avoided by the present process.

A particular advantage of the process is that the reactor parts on which coked and/or silicified deposits customarily form, in particular reactor walls, evaporation and heating surfaces, are continuously cleaned by the fluidized particles and coked and silicified particles can be ejected and replaced or regenerated without interrupting the process.

The particles can be regenerated at temperatures of 150 to 800° C., preferably 200 to 600° C., more preferably in a range of 400 to 500° C., and at a pressure of $0.01 \cdot 10^5$ Pa to $100 \cdot 10^5$ Pa, more preferably at $0.5 \cdot 10^5$ Pa to $10 \cdot 10^5$ Pa.

For the regeneration, the particles can be contacted with reactive gases, liquids or solids. Particular preference is given to regeneration with oxygen-containing gases, in particular with air or lean air (air/nitrogen mixture), the particles preferably being in a fluidized state. The oxygen content in the reaction system of the regeneration is preferably below the oxygen limit concentration to restrict the risk of explosions.

In a preferred embodiment, the particles are regenerated with air in a fluidized bed at 450° C. and $1.5 \cdot 10^5$ Pa.

FIG. 1a describes a possible embodiment and apparatus for carrying out the inventive process having a fluidized bed and batchwise regeneration: carrier gas is fed to the reaction system via the lines (1). The starting material (H) (carbamatoorganosilane) passes into the reaction system via one or more of the lines (2) and is atomized into the fluidized bed (6). In the fluidized bed (6) there are heating elements (4) which are heated by the reactor heaters (5) and maintain and control the reaction temperature. The reaction gas leaves the reactor (A) via the cyclone (8) which separates off particles (fluidized solid particles) and recirculates them into the fluidized bed (6). The reactor pressure is regulated by the valve (9). In the cyclone (10), fine dust fractions are once again separated off. Via the line (11), the reactor exit gas (reaction gas) comprising the crude product (G) passes to workup according to FIG. 3.

During the batchwise regeneration, no further starting material is fed via the lines (2) and first the reactor (A) is purged by inert gas via line (1), and then an oxygen-containing gas is passed via line (7) into the hot reactor (A). The valve (12) is closed and the gas produced in the regeneration is blown off via line (13).

Figure 1B:
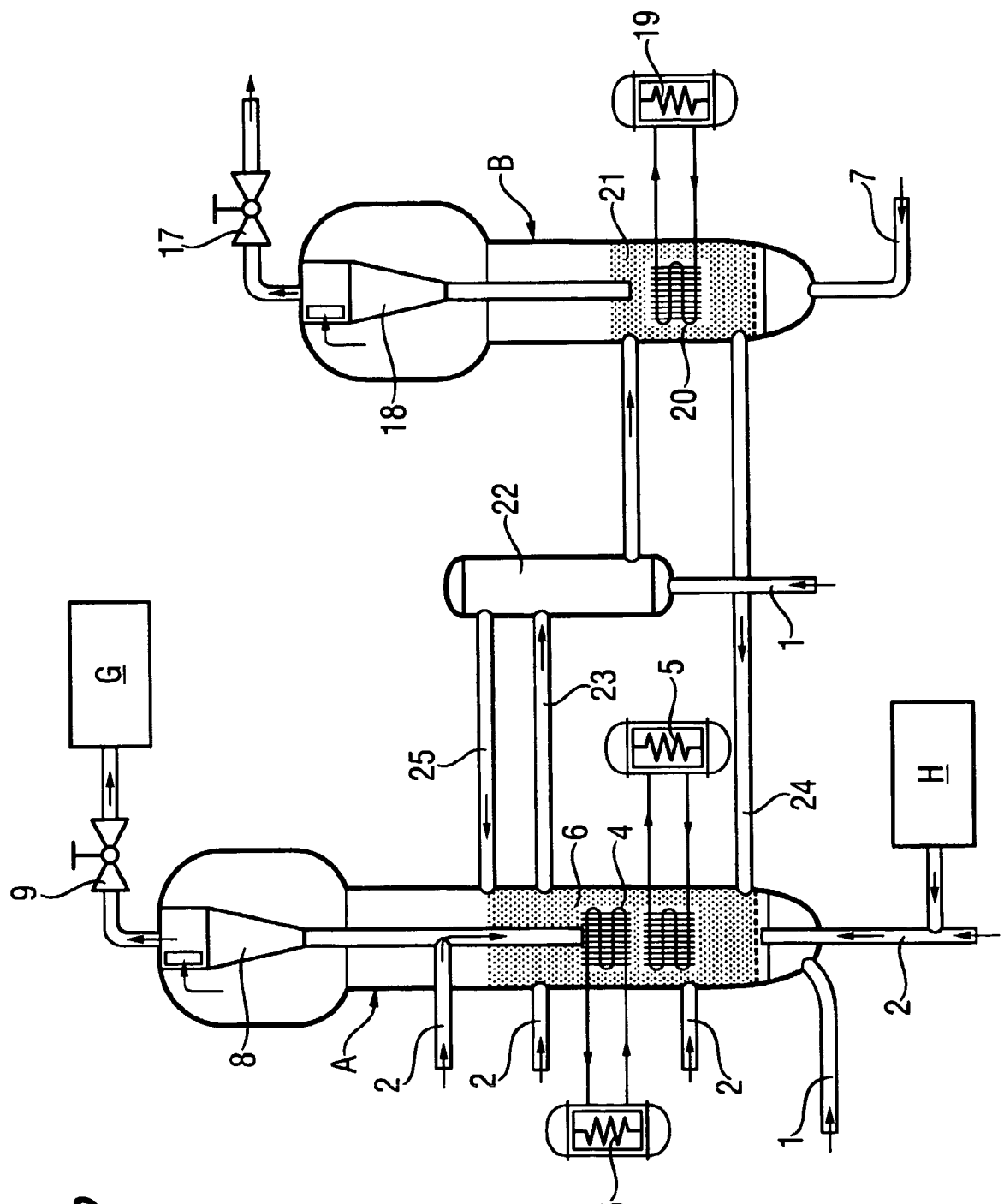

FIG. 1b describes a possible embodiment and apparatus for carrying out the inventive process with fluidized bed and continuous regeneration: carrier gas is fed to the reaction system via the lines (1). Via one or more of the lines (2), the starting material (H) (carbamatoorganosilane) passes into the reaction system and is atomized into the fluidized bed (6). In the fluidized bed (6) there are heating elements (4) which are heated by the reactor heaters (5) and maintain and regulate the reaction temperature. The reaction gas leaves the reactor (A) via the cyclone (8) which separates off particles (fluidized solid particles) and recirculates them to the fluidized bed (6). The reactor pressure is regulated at valve (9). The process following valve (9) and the possible apparatus for isolating the product from the reactor exit gas comprising the crude product (G) (isocyanatoorganosilane) corresponds to that which is described below under FIG. 3.

A part of the solid charge is taken off continuously from the reactor via line (23). The solid is freed in the stripper (22) from adhering volatile starting materials and products and transferred to the regenerator (B). The stripping gases are recirculated to the reaction system via line (25). The regenerator (B) is heated via preheated oxygen-containing regeneration gas which is fed via line (7), and/or via a heater (20) and (19) in the fluidizing zone. The particles taken off from the reactor (A) are treated with an oxygen-containing gas in the fluidized bed (21) of the regenerator (B) and recirculated continuously to the reactor (A) via line (24). The cyclone (18) separates particles from the regeneration gas and recirculates them to the regeneration fluidized bed (21). The valve (17) regulates the regeneration pressure in the regenerator (B).

Figure 1C:
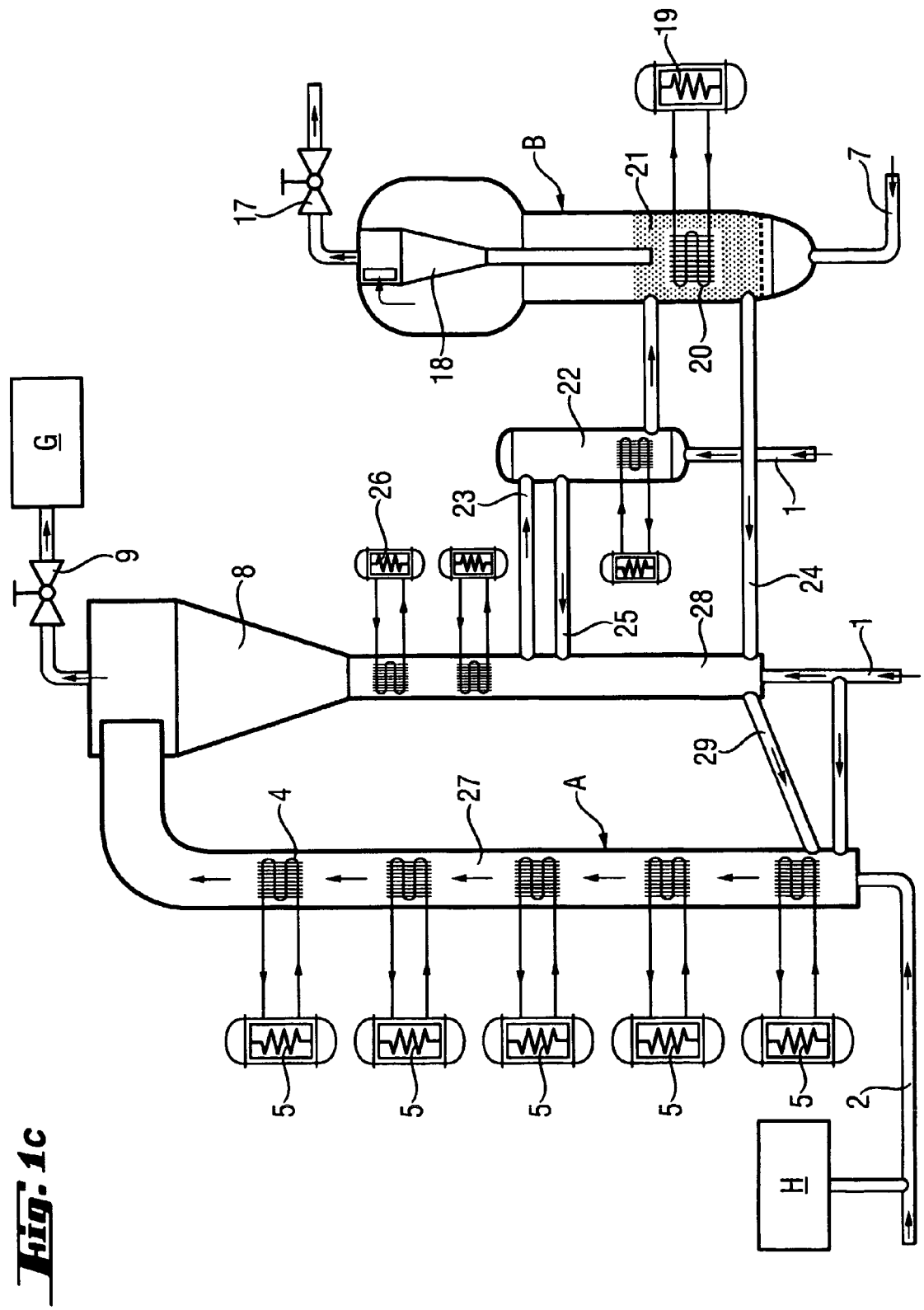

FIG. 1c describes a possible embodiment and apparatus for carrying out the inventive process with a circulating fluidized bed (riser) and regenerator: carrier gas is fed to the reaction system via the lines (1) to the reactor riser pipe (27), to the stand pipe (28) and to the stripper (22). Via line (2), the starting material (H) (carbamatoorganosilane) passes to the reactor (A) and, at the bottom end of the riser pipe (27) of the reactor (A), is atomized into the particles (fluidized solid particles) fed or recirculated via line (29), from the continuous regenerator (B) similar to FIG. 1b. Particles and gas stream rise together through the reactor (A) riser pipe which is heated by one or more heaters (4/5). In the cyclone (8), the particles are separated from the reaction gas and recirculated via the stand pipe (28) the line (29) to the reactor inlet. The reactor pressure is regulated via valve (9). The process following the valve (9) and the possible apparatus for isolating the product (isocyanatoorganosilane) from the stream (G) corresponds to that which is described below under FIG. 3. In the stand pipe (28), the particles are freed from adhering volatile products. A part of the solid charge of the reaction system is continuously taken off via line (23), freed from all volatile compounds in the stripper (22) and treated with an oxygen-containing gas in the fluidized bed (21) of the regenerator (B). The stripping gases are recirculated to the reaction system via line (25). The regenerator (B) is heated via preheated oxygen-containing regeneration gas which is fed via line (7) and/or via a heater (20) and (19) in the fluidized zone (21). The particles which are taken off from the reactor and regenerated are continuously recirculated to the reactor via line (24) and line (29). The cyclone (18) separates particles from the regeneration gas and recirculates them to the regeneration fluidized bed (21). The valve (17) regulates the regeneration pressure.

In a preferred embodiment of the inventive process, in particular that of the embodiments described in FIGS. 1a, 1b and 1c, to complete the reaction, the gaseous effluent stream (G) which can be taken off from the reactor via valve (9) and comprises fluidized solid particles can further be passed into one or more down-stream reactors (post-reactors).

The volume of each secondary reactor can be 0.1 time to 20 times the volume, preferably 0.5 to 5 times the volume, particularly preferably 1 to 3 times the volume of the main reactor.

The secondary reactors can be operated at a temperature of 150 to 800° C., preferably 200 to 600° C., more preferably in a range of 400 to 500° C., and at a pressure of $0.01 \cdot 10^5$ to $100 \cdot 10^5$ Pa, more preferably at $0.5 \cdot 10^5$ to $10 \cdot 10^5$ Pa.

The secondary reactors can have reaction zones corresponding to a mixed vessel or tube. The reaction zones can be furnished with stirring devices, inert internals, e.g. beds of random packings, structured packings or mixer structures. Reactors which are furnished with fluidized particles and/or fluidized heterogeneous catalyst particles or with a fixed heterogeneous catalyst are particularly advantageous.

Figure 2:
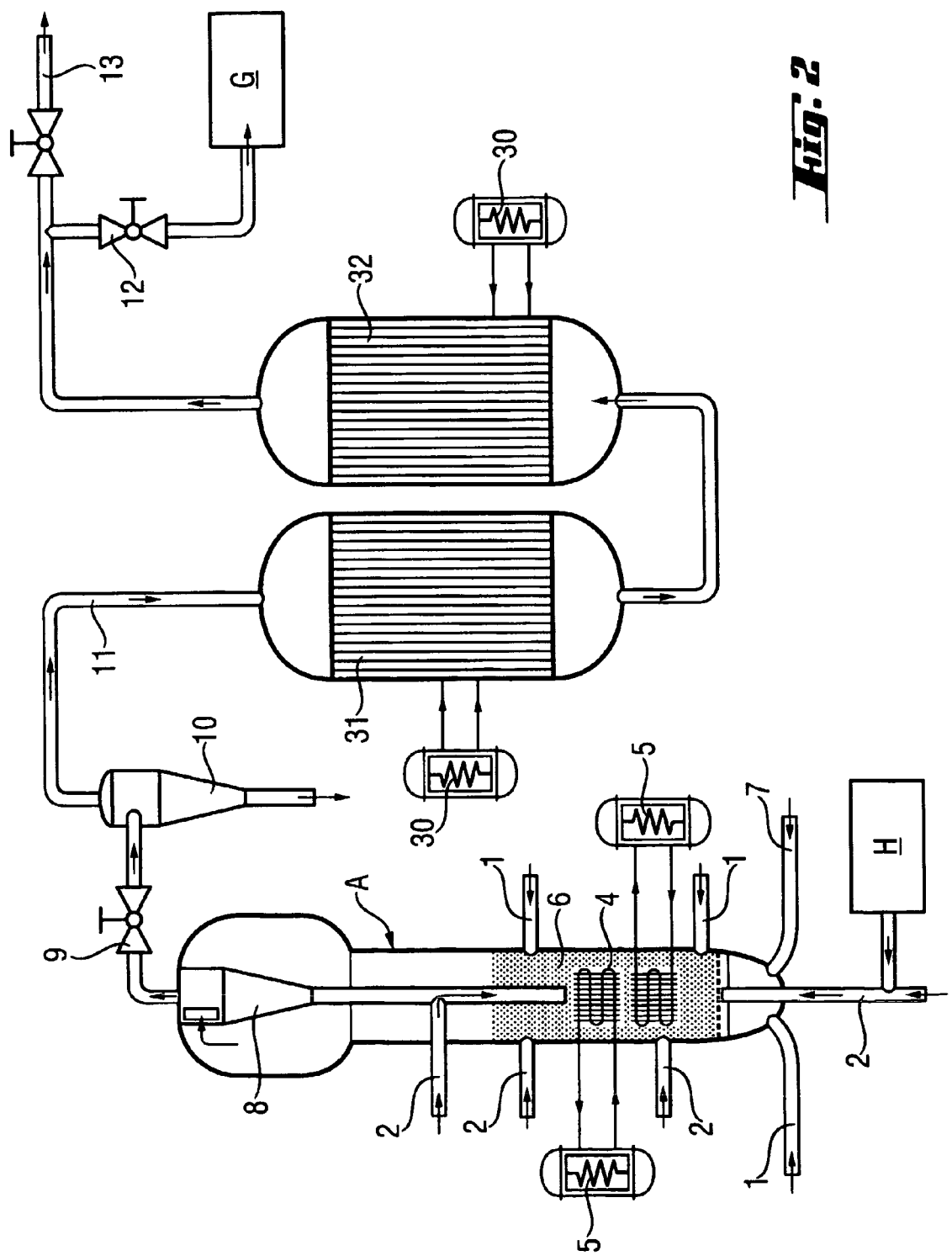
FIG. 2 illustrates further embodiments of a process according to the invention.

FIG. 2 describes an inventive process and a possible apparatus having a main reactor and post-reactor: the reaction gas leaving the first reactor (main reactor), for example a reactor which is designed according to the process described in FIG. 1a, is fed via line (11) to the first post-reactor (31). In the first post-reactor (31) the reaction gas is further reacted at a temperature which is established and regulated by the heater (30) and at a pressure established and regulated by the natural pressure drop and the valve (12). The reaction gas of the first post-reactor is then reacted further in the second post-reactor (32).

The batchwise regeneration is performed in this case in a similar manner to the process described in FIG. 1a: thus, no further starting material is fed via the lines (2) and first the reactor (A) is purged with inert gas via line (1) and then an oxygen-containing gas is passed via line (7) into the hot reactor (A). The valve (12) is closed and the gas produced in the regeneration is blown off via line (13).

FIG. 3 shows in general an embodiment and apparatus for the inventive product workup which can be connected to all embodiments according to FIGS. 1a, 1b, 1c, 2, in which case the streams (G) and (H) denote the respective interfaces to the abovementioned figures. The stream (G) comprising the crude product is freed overhead, in a stripping column (14), from low boilers and gases (B), in particular the alcohol eliminated in the thermolysis, by feeding a stripping gas (E). A stream freed from the low boilers is passed from the bottom of the stripping (14) to a downstream column (15), in which case the pure isocyanatoorganosilane (C) is produced overhead and via the bottom a high-boiler mixture comprising unreacted carbamatoorganosilane (D) is separated off. This can be recirculated (H) in part or completely, via the pump (16) to the system start, optionally after a further chemical or physical treatment or workup.

The stream (H) corresponds in all of the possible embodiments of the inventive process shown in FIGS. 1a, 1b, 1c and 2 to a stream comprising carbamatoorganosilane produced from the workup.

Suitable stripping gases (E) are generally selected from the group consisting of nitrogen, noble gases, carbon dioxide, low-boiling hydrocarbons, e.g. methane, ethane, propane, butane, pentane etc., or mixtures with other substances which are gaseous under the stripping conditions and which comprise one or more of these components in fractions greater than 50%.

COMPARATIVE EXAMPLE 1

2.1 mol of methylcarbamatopropyltrimethoxysilane were heated and vaporized in the course of 2 h in an electrically heated boiling flask. The vapor was passed into an electrically heated, catalyst-filled tubular reactor having an internal diameter of 25 mm and reacted to form γ-isocyanatopropyltrimethoxysilane. The gas mixture leaving the tubular reactor was cooled in a glass Liebig condenser (length 200 mm). The temperature of the tubular reactor was 450° C. at a pressure of 1·10$^5$ Pa at the system outlet, downstream of the condenser. The tubular reactor was charged with a catalyst consisting of a magnesium-oxide-coated, straight-channeled cordierite monolith (2MgO.2Al$_2$O$_3$.5SiO$_2$). Starting from 2.1 mol of methylcarbamatopropyltrimethoxysilane, in the condensate downstream of the condenser, 1.18 mol of γ-isocyanatopropyltrimethoxysilane and 0.33 mol of unreacted methylcarbamatopropyltrimethoxysilane were found. This corresponds to a γ-isocyanatopropyltrimethoxysilane yield of 56% with respect to methylcarbamatopropyltrimethoxysilane used. In the electrically heated boiling flask used for the evaporation, there remain 98 g of oligomeric and polymeric residues, which are not further utilizable, from the thermally induced decomposition of the methylcarbamatopropyltrimethoxysilane.

EXAMPLE 1

Reaction

In a similar manner to a process according to FIG. 2, methylcarbamatopropyltrimethoxysilane was metered into a fluidized bed of 50 g of Fe$_2$O$_3$ granules (55 μm mean particle size) in a glass reactor at a rate of 16 ml/min. The reactor temperature was regulated at 250° C. by irradiation with microwaves of frequency 2.45 GHz and a microwave power of a maximum of 800 W. The particles were prefluidized using a nitrogen stream of 75 l(S.T.P.)/h. The heating/vaporization/reaction of the methylcarbamatopropyltrimethoxysilane in the fluidized bed took place at a pressure of 1·10$^5$ Pa. The vapor leaving the fluidized bed reactor was, to complete the conversion rate, passed into an electrically heated catalyst-charged tubular reactor having a 25 mm internal diameter and further reacted to form γ-isocyanatopropyltrimethoxysilane. The gas mixture leaving the tubular reactor was cooled to 25° C. The temperature of the tubular reactor was 440° C. at a pressure of 1·10$^5$ Pa. The tubular reactor was charged with a catalyst consisting of an Fe$_2$O$_3$-coated, straight-channeled cordierite monolith (2MgO.2Al$_2$O$_3$.5SiO$_2$). Starting from 4.07 mol of methylcarbamatopropyltrimethoxysilane, 3.04 mol of γ-isocyanatopropyltrimethoxysilane and 0.7 mol of unreacted methylcarbamatopropyltrimethoxysilane were found in the condensate downstream of the condenser. This corresponds to a total conversion of methylcarbamatopropyltrimethoxysilane of 83% and a γ-isocyanatopropyltrimethoxysilane yield of 75%, with respect to methylcarbamatopropyltrimethoxysilane used.

EXAMPLE 2

Regeneration

With increasing reaction time and deposition of decomposition products onto the particles, the fluidization characteristics of the particles become impaired.

Used Fe$_2$O$_3$ particles from Example 1 were regenerated in a quartz tube in a fluidized bed at 450° C. For fluidization and regeneration, a gas stream consisting of 500 l(S.T.P.)/h of air and 250 l(S.T.P.)/h of nitrogen was used. After a regeneration time of 2 h, the regenerated Fe$_2$O$_3$ particles were used instead of fresh Fe$_2$O$_3$ particles in an experiment similar to Example 1. Table 1 compares the result obtained using the regenerated particles using fresh particles.

TABLE 1

| Fe$_2$O$_3$ particles | Conversion rate of methylcarbamato-propyltrimethoxy-silane | Yield of γ-isocyanato-propyltrimethoxy-silane |
|---|---|---|
| fresh | 83% | 75% |
| regenerated | 83% | 73% |

The invention claimed is:

1. A process for preparing isocyanatoorganosilanes, comprising thermolyzing at least one carbamatoorganosilane in the presence of fluidized solid particles.

2. The process of claim 1, wherein isocyanatoorganosilanes of the formula (1) are prepared $$R^2R^3R^4Si\text{—}R^1\text{—}N\text{=}C\text{=}O \qquad (1),$$

where
R is a monovalent $C_1$-$C_{10}$-alkyl radical,
$R^1$ is a divalent $C_1$-$C_6$-hydrocarbon radical and
$R^2$, $R^3$ and $R^4$ are in each case independently of one another, a methyl, ethyl, n-propyl, isopropyl, methoxy, ethoxy, n-propoxy or isopropoxy radical, by thermolyzing carbamatoorganosilane of the formula (2)

$$R^2R^3R^4Si\text{---}R^1\text{---}NH\text{---}CO\text{---}OR \qquad (2),$$

in the presence of fluidized solid particles.

3. The process of claim 1, wherein thermolyzing takes place in the presence of a catalyst.

4. The process of claim 2, wherein thermolyzing takes place in the presence of a catalyst.

5. The process of claim 1, wherein the solid particles have a size between 1 10−6 m and 1 10−2 m.

6. The process of claim 2, wherein the solid particles have a size between 1 10−6 m and 1 10−2 m.

7. The process of claim 1, wherein 1% to 100% of the fluidized solid particles consist of a catalyst or a combination of a plurality of heterogeneous catalysts.

8. The process of claim 2, wherein 1% to 100% of the fluidized solid particles consist of a catalyst or a combination of a plurality of heterogeneous catalysts.

9. The process of claim 1, wherein the starting material is introduced into the reaction system via atomization.

10. The process of claim 2, wherein the starting material is introduced into the reaction system via atomization.

11. The process of claim 1, wherein at least one of the fluidized solid particles, the catalyst, precursor compounds of the catalyst, or fluidized solid particles are fed as solution, sol, gel, emulsion, suspension, melt, vapor or solid to the reaction system, batchwise or continuously, mixed with the starting material or separately, at one or more points of the reaction system.

12. The process of claim 1, wherein energy is fed to at least one of the reaction system or the fluidized particles, by steam, thermal oil, liquid or vaporous synthetic heat carriers, liquid salt mixtures, liquid metal alloys, hot gases, electrical resistance heating or microwave heating.

13. The process of claim 1, wherein, batchwise or continuously, fresh particles and/or catalyst are fed, a corresponding fraction of used particles is removed from the reaction system.

14. The process of claim 2, wherein, batchwise or continuously, fresh particles and/or catalyst are fed, a corresponding fraction of used particles is removed from the reaction system.

15. The process of claim 9, wherein, batchwise or continuously, fresh particles and/or catalyst are fed, a corresponding fraction of used particles is removed from the reaction system.

16. The process of claim 1, wherein the effluent stream from the reactor comprising the crude products is passed into one or more post-reactors.

17. The process of claim 2, wherein the effluent stream from the reactor comprising the crude products is passed into one or more post-reactors.

18. The process of claim 8, wherein the effluent stream from the reactor comprising the crude products is passed into one or more post-reactors.

19. The process of claim 14, wherein the effluent stream from the reactor comprising the crude products is passed into one or more post-reactors.

20. The process of claim 1, wherein said fluidized particles are heated by irradiation with microwave energy.

* * * * *